(12) United States Patent
Brammer et al.

(10) Patent No.: US 7,906,688 B2
(45) Date of Patent: Mar. 15, 2011

(54) CALIXARENE BISPHOSPHITE LIGAND FOR USE IN HYDROFORMYLATION PROCESSES

(75) Inventors: Michael A. Brammer, Lake Jackson, TX (US); Wei-Jun Peng, Midland, MI (US); John M. Maher, Charleston, WV (US)

(73) Assignee: Dow Global Technologies Inc.

( * ) Notice: Subject to any disclaimer, the term of this patent is extended or adjusted under 35 U.S.C. 154(b) by 0 days.

(21) Appl. No.: 12/593,296

(22) PCT Filed: Apr. 3, 2008

(86) PCT No.: PCT/US2008/059216
§ 371 (c)(1),
(2), (4) Date: Nov. 13, 2009

(87) PCT Pub. No.: WO2008/124468
PCT Pub. Date: Oct. 16, 2008

(65) Prior Publication Data
US 2010/0044628 A1  Feb. 25, 2010

Related U.S. Application Data

(60) Provisional application No. 60/921,945, filed on Apr. 5, 2007.

(51) Int. Cl.
C07C 45/50 (2006.01)
C07F 9/02 (2006.01)
B01J 31/00 (2006.01)
(52) U.S. Cl. ............ 568/454; 568/12; 502/167
(58) Field of Classification Search .......... 568/12, 568/454; 502/167
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,247,486 A | 1/1981 | Brewester et al. |
| 4,969,953 A | 11/1990 | Miyazawa et al. |
| 5,717,126 A | 2/1998 | Paciello et al. |
| 5,929,289 A | 7/1999 | Abatjoglou et al. |
| 2007/0112220 A1 | 5/2007 | Caers et al. |

OTHER PUBLICATIONS

Steyer et al. Bis-phosphites and bis-phosphinites based on distally-functionalised calix[4]arenes: coordination chemistry and use in rhodium-catalysed, low pressure hydroformylation. Dalton Transactions, 2005, 1301-1309.*
Semeril et al. Regioselectivity with Hemispherical Chelators: Increasing the Catalytic Efficiency of Complexes of Diphosphanes with Large Bite Angles. Angewandte Chem. International Ed., 2006, vol. 45, 5810-5814.*
Kunze et al. Synthesis of New Calix[4]arene-Based Phosphorus Ligands and Their Application in the Rh(I) Catalyzed Hydroformylation of 1-Octene. Heteroatom Chemistry, 2001, vol. 12 (7) 577-585.*
Shirakawa et al. Rhodium-catalyzed bisphasic hydroformylation of 4-octene using water-soluble calix[4]arene-phosphine ligands. New Journal of Chemistry, 2001, vol. 25, 777-779.*
Paciello et al. Chelated Bisphosphites with a Calix[4]arene Backbone: New Ligands for Rhodium-Catalyzed Low-Pressure Hydroformylation with Controlled Regioselectivity. Angewandte Chem. International Edition, 1999, vol. 38 (13/14), 1920-1923.*
Cobley et al., Rhodium(I) complexes of robust phosphites derived from calis[4]arenes and their application in the hydroformylation of 1-hexene., J. Chem. Soc., Dalton Trans., 2000, 1109-1112.
Kunze et al., Calix[4]arene-based Bis-phosphonites, Bis-phosphites, and Bis-O-acyl-phosphites as Ligands in the Rhodium(I)-catalyzed Hydroformylation of 1-Octene., Z. Anorg. Allg. Chem. 2002, 628, 779-787.

* cited by examiner

*Primary Examiner* — Sikarl A Witherspoon
(74) *Attorney, Agent, or Firm* — Marie F. Zuckerman; Paul D. Hayhurst (57) ABSTRACT

A calixarene bisphosphite composition for use as a ligand in a transition metal-ligand complex catalyst and in a complex catalyst precursor. The ligand is especially useful in catalysts and catalyst precursors for hydroformylation processes wherein a raffinate stream comprising a mixture of alpha, beta, and iso-olefinic isomers is hydroformylated in the presence of carbon monoxide, hydrogen, and the transition metal-ligand complex catalyst to form a mixture of linear and branched aldehyde products. The complex catalyst selectively converts the alpha and beta olefin reactants more rapidly than the iso-olefin reactant resulting in an improved molar ratio of normal (linear) to branched aldehyde products. The unconverted iso-olefinic isomer is thereafter readily separated from the aldehyde product mixture.

20 Claims, 2 Drawing Sheets

CALIXARENE BISPHOSPHITE LIGAND FOR USE IN HYDROFORMYLATION PROCESSES

CROSS REFERENCE TO RELATED APPLICATIONS

This application is a 371 of PCT/US2008/059216 filed Apr. 3, 2008, which claims the benefit of U.S. Provisional Application Ser. No. 60/921,945, filed Apr. 5, 2007.

BACKGROUND OF THE INVENTION

This invention relates to a novel calixarene bisphosphite composition and its use in transition metal complex-catalyzed hydroformylation processes. As used herein, the term "hydroformylation" refers to a process of reacting one or more olefins with carbon monoxide and hydrogen in the presence of a hydroformylation catalyst to prepare one or more aldehyde products.

One important class of hydroformylation processes involves using a C4 butene stream as a raw material for hydroformylation to obtain C5 aldehydes, preferably, n-valeraldehyde. In some commercial operations, valeraldehyde is dimerized, and the dimerization product is hydrogenated to produce 2-propylheptanol or a mixture thereof with other alcohols, which find utility in the production of plasticizers. Alternatively, valeraldehyde may be hydrogenated to produce pentanol or amyl alcohol or mixtures of different C5 alcohol isomers thereof, any of which alcohols or alcohol mixtures may be used as a solvent. Valeraldehyde may also be oxidized to produce valeric acid or isomeric mixtures thereof, which may be used in synthetic ester lubricant products.

In the chemical art, the term "butene" or "butylene" generically refers to all hydrocarbon compounds having four carbon atoms and one carbon-carbon unsaturated double bond. Examples of specific butenes include butene-1, butene-2 (which includes cis and trans isomers), and isobutene (or isobutylene).

C5 aldehydes, such as valeraldehyde, are typically prepared by the hydroformylation of polymer grade butene-1, which is obtained through cracking petroleum and extensive purification procedures. In contrast, C4 raffinate feedstocks are a plentiful, less expensive source of C4 olefins as compared with polymer grade butene-1. As used herein, the term "C4 raffinate" or "C4 raffinate feedstock" refers to a C4 feedstream comprising a mixture of butene-1, butene-2 (cis and trans isomers), and isobutene. C4 raffinate feedstocks are obtained by thermal or catalytic cracking of hydrocarbon oils with subsequent treatment to remove butadiene, but otherwise with far less purification as is needed for polymer grade butene-1. Consequently, it would be advantageous to employ a C4 raffinate feedstock rather than polymer grade butene-1 in hydroformylation processes.

n-Valeraldehyde, which is a normal or linear product derived from butene-1, is preferred for many downstream end-uses. In contrast, due to branching, 3-methylbutyraldehyde, derived from isobutene, is an undesirable product, because it imparts inferior qualities to downstream products, particularly plasticizers. 2-Methylbutyraldehyde derived from butene-2 is an acceptable product. Moreover, at least a portion of butene-2 can be isomerized under hydroformylation reaction conditions to butene-1, which yields more of the normal or linear isomeric product. Given the effects on downstream products, it is advantageous to maximize the isomer ratio of normal to branched aldehydes (normal/branched or N:I isomer ratio) in the hydroformylation product stream.

The art, for example, WO-A1-2005/028407, discloses a hydroformylation of C4 raffinate feedstocks in the presence of a transition metal-organophosphorus ligand complex catalyst, wherein the ligand consists of an organophosphine or an organobisphosphite compound, to produce a product mixture comprising n-valeraldehyde, 2-methyl-butyraldehyde, and 3-methylbutyraldehyde. When isobutene is a significant component of the C4 raffinate feedstream (e.g., greater than 1 volume percent), typically, the N:I isomer ratio achieved is unacceptably low (<3/1). Moreover, insofar as is taught in WO 2005/028407, the rate of conversion of butene-2 is essentially identical to the rate of conversion of isobutene, which limits the extent to which the N:I isomer ratio can be improved.

One method of maximizing the N:I isomer ratio in the hydroformylation product involves removing undesirable 3-methylbutyraldehyde from the hydroformylation product stream; however, selective removal of one isomer from an isomeric mixture comprising valeraldehyde, 2-methylbutyraldehyde, and 3-methylbutyraldehyde involves difficult and expensive procedures.

Another method of maximizing the N:I product isomer ratio involves removing from the C4 raffinate feedstock the isobutene reactant from which the problematical 3-methylbutyraldehyde is derived. U.S. Pat. No. 4,969,953 discloses the hydroformylation of raffinate I streams pretreated to remove butadiene as well as raffinate II streams pretreated to remove butadiene and isobutene. As the concentration of isobutene in the feedstream is lowered, the aldehyde product N:I isomer ratio is shown to increase. The skilled person generally recognizes that removing isobutene from a C4 raffinate is also a difficult and expensive procedure and, thus, also impractical.

In contrast to the above, separation of unconverted isobutene from a hydroformylation product mixture comprising C5 product aldehydes could be more readily achieved. Consequently, a need exists in the art for a catalyst that is capable of hydroformylating a C4 raffinate feedstock with increased conversion of butene-1 and butene-2 as compared with isobutene. Such a process would increase the N:I product isomer ratio while providing for reduced conversion of isobutene. The resulting hydroformylation product would comprise valeraldehyde, 2-methyl-butyraldehyde, unconverted olefins, primarily isobutene, and a reduced quantity of 3-methylbutryaldehyde. The separation of unconverted isobutene from the aforementioned hydroformylation product would be simple and cost effective.

The prior art discloses phosphorus-containing calixarenes and their use in hydroformylating a single olefin isomer, such as 1-octene, to the corresponding aldehyde, such as n-nonanal. Such art includes U.S. Pat. No. 5,717,126, as well as S. Steyer, et al., *Dalton Transactions*, 2005, 1301-1309; and C. Kunze, et al., *Z. Anorg. Allg. Chem.*, 2002, 628, 779-787.

SUMMARY OF THE INVENTION

In one aspect, this invention provides for a hydroformylation process comprising contacting a reactant mixture comprising isomeric olefins represented by the following formulas:

$$RCH_2-C(CH_3)=CH_2 \text{(hereinafter, iso-olefin reactant)} \quad (III)$$

wherein each R is the same and is selected from the group consisting of hydrogen and $C_{1-4}$ monovalent alkyl radicals, with carbon monoxide and hydrogen in the presence of a transition metal-calixarene bisphosphite ligand complex catalyst, and optionally free calixarene bisphosphite ligand, under reaction conditions sufficient to form a hydroformylation product mixture comprising corresponding normal and branched isomeric aldehyde products. Moreover, in the process of this invention the α-olefin and β-olefin reactants achieve a conversion of greater than about 1.5 times the conversion of the iso-olefin reactant. In this invention, the calixarene bisphosphite ligand is represented by the following formula:

(IV)

wherein the calixarene is a calix[4]arene; each $R^1$, $R^2$, $R^3$, and $R^4$ is independently selected from the group consisting of hydrogen and substituted or unsubstituted alkyl radicals; each $Y^1$ and $Y^2$ is independently selected from the group consisting of substituted and unsubstituted monovalent alkyl, alkaryl, aralkyl, and amide radicals; and wherein each $Ar^1$, $Ar^2$, $Ar^3$, and $Ar^4$ is independently selected from substituted and unsubstituted monovalent aryl radicals, or alternatively, wherein $Ar^1$ and $Ar^2$ are connected to form a substituted or unsubstituted divalent arylene radical and/or $Ar^3$ and $Ar^4$ are connected to form a substituted or unsubstituted divalent arylene radical.

The process of this invention advantageously provides for hydroformylating a mixture of α-olefin, β-olefin and iso-olefin isomers, preferably, a C4 raffinate feedstock comprising a mixture of butene-1, butene-2 (cis and trans isomers), and isobutene. Moreover, the process of this invention achieves a higher conversion of α-olefin and β-olefin reactants as compared with the iso-olefin reactant. Accordingly, the process of this invention is particularly suited for hydroformylating a raffinate feedstock to an aldehyde product mixture having an improved normal/branched (N:I) isomer product ratio. For example, the process of this invention can be used with the aforementioned C4 raffinate feedstock to produce a product mixture comprising valeraldehyde, 2-methylbutyraldehyde, and 3-methylbutyraldehyde having an improved N:I isomer ratio, as compared with prior art processes employing C4 raffinate feedstocks having a comparable isobutene concentration. Moreover, the separation of iso-olefin, preferably isobutene, from the aldehyde reaction product is easily accomplished.

In a second aspect, this invention provides for a novel calixarene bisphosphite composition represented by the following formula:

(V)

wherein the calixarene is a calix[4]arene; each $R^1$, $R^2$, $R^3$, and $R^4$ is independently selected from the group consisting of hydrogen and substituted or unsubstituted monovalent alkyl radicals; each $Y^1$ and $Y^2$ is independently selected from the group consisting of substituted and unsubstituted monovalent alkyl, alkaryl, aralkyl, and amide radicals; and each $R^5$, $R^6$, $R^7$, $R^8$, $R^9$, $R^{10}$, $R^{11}$, $R^{12}$, $R^{5'}$, $R^{6'}$, $R^{7'}$, $R^{8'}$, $R^{9'}$, $R^{10'}$, $R^{11'}$, $R^{12'}$ is independently selected from hydrogen, alkyl, alkaryl, alkoxy, aryloxy, keto, carbonyloxy, and alkoxycarbonyl groups.

The novel calixarene bisphosphite composition of this invention finds utility as a ligand in transition metal-ligand complex catalyst and catalyst precursor compositions that are used in hydroformylation processes.

In a third aspect, this invention provides for a novel complex catalyst or complex catalyst precursor composition comprising a transition metal bonded to a calixarene bisphosphite ligand represented by formula V hereinabove, the transition metal optionally being further bonded to carbon monoxide, hydrogen, or both carbon monoxide and hydrogen.

In a fourth aspect, this invention provides for a complex catalyst solution or complex catalyst precursor solution comprising a solvent, a complex catalyst or catalyst precursor composition comprising a transition metal bonded to a novel calixarene bisphosphite ligand, and optionally, free calixarene bisphosphite ligand, the aforementioned calixarene ligand being represented by formula V hereinabove; and wherein optionally, the transition metal may be further bonded to carbon monoxide, hydrogen, or both carbon monoxide and hydrogen.

The aforementioned catalyst and catalyst precursor compositions and solutions thereof find utility in hydroformylation processes. As compared with prior art hydroformylation catalysts, the novel calixarene bisphosphite ligand-containing catalyst provides for unexpectedly higher conversion of terminal (α) and internal (β) olefin isomers, as compared with the iso-olefin isomer. Moreover, the calixarene bisphosphite ligand-containing catalyst of this invention provides for a higher N:I product isomer ratio, as compared with prior art catalysts.

DETAILED DESCRIPTION OF THE INVENTION

The invention described herein is advantageously applicable to the hydroformylation of raffinate feedstocks comprising α-olefin, β-olefin, and iso-olefin reactants, achieving therein a greater conversion of the α-olefin and β-olefin isomers as compared with the iso-olefin isomer. In this aspect, the invention provides for a hydroformylation process comprising contacting a mixture comprising isomeric olefins represented by the following formulas:

$RCH_2—CH_2—CH=CH_2$(hereinafter,α-olefin reactant)      (I), $RCH_2—CH=CH—CH_3$(hereinafter,β-olefin reactant)      (II), and $RCH_2—C(CH_3)=CH_2$(hereinafter,iso-olefin reactant)      (III)

wherein each R is the same and is selected from the group consisting of hydrogen and $C_{1-4}$ monovalent alkyl radicals, with carbon monoxide and hydrogen in the presence of a transition metal-calixarene bisphosphite ligand complex catalyst, and optionally free calixarene bisphosphite ligand, under reaction conditions sufficient to form a hydroformylation product mixture comprising corresponding normal and branched isomeric aldehyde products. Moreover, in the process of this invention the α-olefin and β-olefin reactants achieve a conversion of greater than about 1.5 times the conversion of the iso-olefin reactant, the conversions preferably being measured on the individual isomers under identical measurement conditions as described hereinafter. In this invention, the calixarene bisphosphite ligand is represented by formula IV, reproduced hereinafter:

(IV)

wherein the calixarene is a calix[4]arene; each $R^1$, $R^2$, $R^3$, and $R^4$ is independently selected from the group consisting of hydrogen and substituted or unsubstituted alkyl radicals, preferably, $C_{1-20}$ alkyl, and more preferably, tert-butyl; each $Y^1$ and $Y^2$ is independently selected from the group consisting of substituted and unsubstituted monovalent alkyl, alkaryl, aralkyl, and amide radicals, preferably, —$CH_2C(O)NR^{13}R^{14}$, —$C(O)NR^{13}R^{14}$, and —$CH_2Ar$, wherein $R^{13}$ and $R^{14}$ are each independently selected from substituted and unsubstituted monovalent alkyl and aryl radicals, more preferably, substituted or unsubstituted monovalent $C_{1-10}$ alkyl and $C_{6-20}$ aryl radicals, and Ar is a substituted or unsubstituted monovalent aryl radical, more preferably, a $C_{6-20}$ substituted or unsubstituted monovalent aryl radical; and wherein each $Ar^1$, $Ar^2$, $Ar^3$, and $Ar^4$ is independently selected from substituted and unsubstituted monovalent aryl radicals, preferably, $C_{6-20}$ substituted or unsubstituted monovalent aryl radicals, or alternatively, wherein $Ar^1$ and $Ar^2$ are connected to form a substituted or unsubstituted divalent arylene radical and/or $Ar^3$ and $Ar^4$ are connected to form a substituted or unsubstituted divalent arylene radical, preferably, in both instances a $C_{12-25}$ substituted or unsubstituted divalent arylene radical.

In a preferred embodiment, the calixarene bisphosphite composition comprises a compound represented by formula V, reproduced hereinafter:

(V)

wherein the calixarene is a calix[4]arene; wherein $R^1$, $R^2$, $R^3$, $R^4$, $Y^1$ and $Y^2$ are identified hereinbefore; and wherein $R^5$, $R^6$, $R^7$, $R^8$, $R^9$, $R^{10}$, $R^{11}$, $R^{12}$, $R^{5\prime}$, $R^{6\prime}$, $R^{7\prime}$, $R^{8\prime}$, $R^{9\prime}$, $R^{10\prime}$, $R^{11\prime}$, $R^{12\prime}$ are each independently selected from hydrogen, alkyl, alkaryl, alkoxy, aryloxy, keto, carbonyloxy, and alkoxycarbonyl, preferably, from hydrogen, $C_{1-20}$ alkyl, $C_{7-20}$ alkaryl, $C_{1-20}$ alkoxy, $C_{6-20}$ aryloxy, —$C(O)R^{15}$, —$C(O)OR^{15}$ and —$OC(O)R^{15}$ wherein $R^{15}$ is a substituted or unsubstituted monovalent $C_{1-15}$ alkyl or monovalent $C_{6-15}$ aryl group. Preferably, the ortho positions on the aryl rings represented by $R^5$, $R^{5\prime}$, $R^{12}$, and $R^{12\prime}$ are each individually selected from hydrogen and $C_{1-3}$ primary alkyl groups.

In a most preferred embodiment, the calixarene bisphosphite ligand comprises N,N-diethylacetamide-p-tert-butyl-calix[4]arene bisphosphite which is represented by the following formula (Va):

(Va)

In a third aspect, this invention provides for a novel complex catalyst or complex catalyst precursor composition comprising a transition metal bonded to a calixarene bisphosphite composition represented by formula V hereinabove, the transition metal optionally being further bonded to carbon monoxide, hydrogen, or both carbon monoxide and hydrogen.

In a fourth aspect, this invention provides for a complex catalyst solution or complex catalyst precursor solution comprising a solvent, a complex catalyst or catalyst precursor composition comprising a transition metal bonded to a calixarene bisphosphite ligand, and optionally, free calixarene bisphosphite ligand, the calixarene ligand being represented by formula V hereinabove; and wherein optionally, the transition metal may be further bonded to carbon monoxide, hydrogen, or both carbon monoxide and hydrogen.

The preparation of the calixarene bisphosphite composition is readily implemented in a three-step synthesis. In a first step, a substituted or unsubstituted phenol or bisphenol is reacted with phosphorus trichloride ($PCl_3$) to prepare a diaryl or arylene phosphoromonochloridite represented by formula VI:

(VI)

wherein $Ar^1$ and $Ar^2$ are defined hereinabove as independently selected from substituted and unsubstituted monovalent aryl radicals, preferably, $C_{6-20}$ substituted or unsubstituted monovalent aryl radicals, or alternatively, wherein $Ar^1$ and $Ar^2$ are connected to form a substituted or unsubstituted divalent arylene radical, preferably, a $C_{12-25}$ substituted or unsubstituted divalent arylene radical. Stoichiometrically, the reaction consumes two moles of phenol per mole of phosphorus trichloride or one mole of bisphenol per mole of phosphorus trichloride. Typically, a molar excess of phosphorus trichloride is employed per mole of (bis)phenol; for example, a 1.5 to 4-fold molar excess of phosphorus trichloride is preferred. The reaction may be conducted in neat (bis)phenol or in a non-reactive solvent that solubilizes the (bis)phenol and phosphorus trichloride reagents without interfering with the reaction. Suitable solvents include, for example, ethers, alkanes, and aromatic hydrocarbons. If used, the solvent is preferably selected from tetrahydrofuran, diethyl ether, toluene, and mixtures thereof. Typically, the reaction is conducted at a temperature greater than about −40° C., and preferably, greater than about −10° C. The maximum temperature is typically at the reflux temperature of the (bis)phenol or the solvent, and preferably, is less than about 120° C., more preferably, less than about 95° C. Generally, the process is carried out at ambient pressure, but a higher or lower pressure may be employed if desired. Reaction under an inert atmosphere, such as nitrogen, argon, or helium, is preferred to avoid contact with oxygen and moisture.

Next, a calix[4]arene tetra-ol (fully hydroxylated) is obtained commercially, e.g. from Aldrich Chemical Company, or is prepared by published literature procedures, as referenced, for example, in *Monographs in Supramolecular Chemistry*, No. 1, "Calixarenes," by C. David Gutsche, Washington University, St. Louis, Mo., 1989, incorporated herein by reference. In a second synthetic step, the calix[4]arene tetra-ol is reacted with a blocking agent, such as an amide, a dialkyl ether, a di(alkylaryl)ether, or a di(arylalkyl)ether, in a molar ratio of 2 moles blocking agent per mole calix[4]arene tetra-ol under reaction conditions sufficient to yield a bis-substituted calix[4]arene diol, wherein the bis substituents block two distal hydroxyl groups. For example, if one mole of the calix[4]arene tetra-ol is reacted with two moles 2-bromo-N,N-diethylacetamide, the resulting product is bis-(N,N-diethylamide)calix[4]arene diol, having N,N-diethylamide substituents blocking two distal hydroxyl groups. "Distal" groups are positioned on opposite or far away sides, rather than at adjacent positions. For example, in a calix[4]arene tetra-ol, the 1,3 hydroxyl positions are distal to each other as are the 2,4 positions; whereas the 1,2 hydroxyl positions are adjacent to each other, as are the 2,3, and 3,4, and 4,1 positions. The bis-substituted calix[4]arene diol can be represented by formula VII hereinbelow:

(VII)

wherein $R^1$, $R^2$, $R^3$, $R^4$, $Y^1$ and $Y^2$ are defined hereinabove.

In the third and final step, the bis-substituted calix[4]arene diol of formula VII is reacted with the diaryl phosphoromonochloridite or arylene phosphoromonochloridite of formula VI, as the case may be, to yield the calix[4]arene bisphosphite composition (IV) of this invention. This third reaction involves contacting the diaryl phosphoromonochloridite or arylene phosphoromonochloridite with the bis-substituted calix[4]arene diol, in a molar ratio of 2:1, respectively, in the presence of an amine base. The two moles of diaryl phosphoromonochloridite may be provided with the same diaryl functionality; i.e., $Ar^1$ and $Ar^2$ are the same pair as $Ar^3$ and $Ar^4$. Alternatively, one mole of a first diaryl phosphoromonochloridite and one mole of a second and different diaryl phosphoromonochloridite may be provided, i.e., the $Ar^1$ and $Ar^2$ pair are different from the $Ar^3$ and $Ar^4$ pair. Suitable, but non-limiting, examples of amine bases include triethylamine, pyridine, and N,N-disubstituted anilines. The quantity of amine base is typically stoichiometric or in excess of one equivalent or more. A solvent may be employed; for example, an ether, ester, or aromatic hydrocarbon is suitably employed. The contacting temperature is typically maintained at the reflux temperature of the solvent. The resulting calixarene bisphosphite composition IV can be identified by conventional analytical techniques known to the skilled person, for example, by elemental analysis (via X-ray fluorescence or neutron activation analysis or atomic absorption), mass spectroscopy, infrared spectroscopy, $^1H$ nuclear magnetic resonance spectroscopy (NMR), $^{13}C$ NMR, and/or $^{31}P$ NMR.

The calixarene bisphosphite composition of this invention finds application as a ligand in metal complex catalysts and catalyst precursors that are used in carbonylation processes, preferably, hydroformylation processes. Accordingly, this invention provides for a class of complex catalysts and complex catalyst precursor compositions that comprise a transition metal bonded to a calixarene bisphosphite ligand represented by formula IV, and preferably, bonded to the calixarene bisphosphite ligand represented by formula V. The transition metal that makes up the complex catalyst or catalyst precursor composition of this invention preferably comprises a Group VIII transition metal, which includes transition metals selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, with the preferred metals being ruthenium, rhodium, cobalt, and iridium, more preferably, rhodium and cobalt, and most preferably, rhodium. The term "complex" as used herein shall mean a coordination compound formed by the union of one or more ligands, in this instance, at least one calixarene bisphosphite ligand, with a transition metal. Inherently, the calixarene bisphosphite ligand is electronically rich compared to the metal, since each ligand possesses two phosphorus (III) donor atoms, each of which possesses one available or unshared pair of electrons that is capable of forming a coordinate covalent bond independently or in concert (e.g., via chelation) with the transition metal. The oxidation state of the metal may be any available oxidation state, both electronically neutral (zero) or electronically deficient (positive valence) that allows for bonding to the calixarene bisphosphite ligand. Moreover, the oxidation state of the transition metal, as well as the overall charges of the coordination complex or complex precursor, may vary during use in the hydroformylation process. The number of available coordination sites on the transition metal is well known in the art and may range typically from about 4 to about 6. Optionally, carbon monoxide and hydrogen may be bonded to the transition metal.

This invention can also be described as a transition metal complex catalyst or catalyst precursor solution comprising an organic solvent, a solubilized transition metal-calixarene bisphosphite ligand complex catalyst, and free calixarene bisphosphite ligand, wherein the ligand is represented by formula IV or preferred formula V hereinabove. Such solutions may be prepared by forming a solution comprising an organic solvent, free calixarene bisphosphite ligand, and a transition metal source material, such as the corresponding transition metal oxide, hydride, carbonyl, salt, or other organotransition metal complex, as described hereinafter; and thereafter subjecting such solution to reaction conditions sufficient to bind at least a portion of the calixarene bisphosphite ligand to the transition metal. Optionally, carbon monoxide and hydrogen may be dissolved in the solution and bonded to the transition metal.

The transition metal-calixarene bisphosphite ligand complex catalyst of this invention can be prepared by methods known in the art. In one instance, the catalyst may be preformed and introduced into the reaction medium of a hydroformylation process. Standard identification methods may be used to identify the complex catalyst or catalyst precursor composition and its ligand components, including for example, elemental analysis, mass spectroscopy, infrared spectroscopy, and $H^1$, $P^{31}$, and/or $C^{13}$ NMR spectroscopy, as known to the skilled person and mentioned above.

Preferably, the transition metal-calixarene bisphosphite ligand complex catalyst of this invention is derived from a transition metal source material that is introduced into the hydroformylation reaction medium to provide for in situ formation of the active catalyst. Preferred are Group VIII source materials; for example, rhodium source materials, such as, rhodium acetylacetonate, rhodium dicarbonyl acetylacetonate, $Rh_2O_3$, $Rh_4(CO)_{12}$, $[RhCl(CO)_2]_2$, $Rh_6(CO)_{16}$, $Rh(NO_3)_3$, and the like may be introduced into the hydroformylation reaction medium along with the calixarene bisphosphite ligand for the in situ formation of the active catalyst. In a preferred embodiment, rhodium dicarbonyl acetylacetonate is employed as a rhodium source and reacted in the presence of a solvent with the calixarene bisphosphite composition to form a catalytic rhodium-calixarene bisphosphite ligand complex precursor composition, which is introduced into the reactor along with excess free calixarene bisphosphite ligand for the in situ formation of the active catalyst. The reaction conditions sufficient for formation of the complex catalyst or catalyst precursor in most cases will be similar to the hydroformylation reaction conditions described hereinbelow.

It is to be noted that the successful practice of this hydroformylation process invention does not depend and is not predicated upon the exact formula of the catalytically active metal complex species, which may be present in a mononuclear, dinuclear, or higher nuclearity form. Indeed, the exact formula of the catalytically active metal ligand complex may be difficult to determine analytically. Although not intended to be bound to any theory or mechanistic discourse, it appears that the active catalytic species in its general form comprises the transition metal in complex combination with one or more calixarene bisphosphite ligands of formula IV, further in combination with carbon monoxide. The catalytically active composition may also contain one or more additional ligands, such as hydrogen, or an anion satisfying the coordination sites or nuclear charge of the transition metal. Illustrative additional ligands include halogen ($Cl^-$, $Br^-$, $I^-$), alkyl, aryl, substituted aryl, $CF_3^-$, $C_2F_5^-$, $CN^-$, $R'_2PO^-$, $R'P(O)(OH)O^-$ (wherein each R' is alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2=CHCH_2^-$, $C_6H_5CN$, $CH_3CH=$, NO, $NH_3$, pyridine, $(C_2H_5)_3N$, mono-olefins, diolefins, triolefins, and tetrahydrofuran.

Any amount of complex catalyst can be employed in the hydroformylation reaction medium, provided that the amount is sufficient to catalyze the desired hydroformylation process. In general, the concentration of complex catalyst provides for a concentration of transition metal of greater than about 10 parts per million (ppm), preferably, greater than about 25 ppm, by weight, calculated as free metal, based on the total weight of the hydroformylation reaction medium. Generally, the concentration of complex catalyst provides for a concentration of transition metal of less than about 1,000 ppm, preferably, less than about 800 ppm, and more preferably, less than about 600 ppm, by weight, calculated as free metal.

The olefin reactant employed in the process of this invention comprises a mixture of α-olefin, β-olefin, and iso-olefin isomers as represented by formulas I, II, and III hereinabove. Preferably, the olefin is a $C_{4-6}$ mono-olefin, more preferably, a $C_4$ olefin (namely, butene), which is present as a C4 raffinate comprising a mixture of butene-1, butene-2 (cis and trans isomers), and isobutene. Preferred raffinate feedstocks for use in the process of the invention comprise the following composition: from about 25 to about 80 percent 1-butene, from about 5 to about 40 percent trans-2-butene, from about 5 to about 25 percent cis-2-butene, from about 0.5 to about 40 percent isobutene, from about 5 to about 20 percent n-butane, and from about 0.5 to 5 percent isobutane, taken on a molar basis. Small quantities of other gases commonly found in mixed-C4 streams, such as 1,3-butadiene, propene, propane, cyclopropane, pentenes, and pentanes, may be present in concentrations of less than 1 mole percent in each case. Note that for the purposes of this invention, the C4 feedstock may contain a low quantity of isobutene (less than 1 mole percent) or a high quantity of isobutene (higher than 1 mole percent up to 40 mole percent), as desired. Thus, this invention is applicable to so-called "raffinate I" feedstocks that have been pretreated to remove butadiene to a concentration of less than 1 mole percent, but otherwise contain a high quantity of isobutene, as well as "raffinate II" feedstocks that have been pretreated to remove butadiene and isobutene to concentrations each less than 1 mole percent.

The hydroformylation process of this invention is preferably conducted in the presence of an organic solvent for the transition metal-calixarene bisphosphite ligand complex catalyst. Any suitable solvent that does not unduly interfere with the hydroformylation process can be used. By way of illustration, suitable solvents for rhodium catalyzed hydroformylation processes include those disclosed, for example, in U.S. Pat. No. 3,527,809; U.S. Pat. No. 4,148,830; and U.S. Pat. No. 5,929,289, the aforementioned citations being incorporated herein by reference. Non-limiting examples of suitable solvents include saturated hydrocarbons, aromatic hydrocarbons, ethers, aldehydes, ketones, nitriles, and aldehyde condensation products. More specific solvents, for example, include the following solvents: tetraglyme, pentanes, cyclohexane, benzene, xylene, toluene, diethyl ether, tetrahydrofuran, butyraldehyde, and benzonitrile. Mixtures of two or more solvents may also be employed. In rhodium catalyzed hydroformylation processes, it may be preferred to employ as a primary solvent aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486, incorporated herein by reference. Indeed, while one may employ, if desired, any suitable solvent at the start-up of a continuous process, the primary solvent will normally eventually comprise both aldehyde products and higher boiling aldehyde liquid condensation by-products, due to the nature of such continuous processes. The amount of solvent is not especially critical and need only be sufficient to provide the reaction medium with the desired amount of transition metal concentration. Typically, the amount of solvent ranges from about 5 percent to about 95 percent by weight, based on the total weight of the hydroformylation reaction fluid.

As a further option, the hydroformylation process of this invention may be conducted in the presence of free calixarene bisphosphite ligand, that is, ligand not complexed to the transition metal. The free calixarene bisphosphite ligand may correspond to any of the calixarene bisphosphite ligand species illustrated hereinabove. While it is preferred to employ a free calixarene bisphosphite ligand that is identical to the calixarene bisphosphite ligand complexed to the transition metal in the transition metal-calixarene bisphosphite complex catalyst, it is not absolutely required for the free and complexed calixarene bisphosphite ligands to be the same; and in fact, they may be different. Typically, at least one mole of free calixarene bisphosphite ligand per mole of transition metal is present in the reaction medium. Preferably, the amount of calixarene bisphosphite ligand per mole of transition metal is greater than about 1.2/1, more preferably, greater than about 1.5/1. Preferably, the amount of calixarene bisphosphite ligand per mole of transition metal is less than about 100/1, more preferably, less than about 50/1. The aforementioned ratios correspond to the sum of both free and complexed calixarene bisphosphite ligand. Make-up calixarene bisphosphite ligand can be added during the carbonylation process at any time and in any suitable manner, so as to maintain a predetermined concentration of free ligand in the reaction medium.

The process conditions for effecting hydroformylation can be chosen from any of those conditions conventionally used and known for such processes. The reaction temperature depends upon the particular olefinic mixture and catalyst employed, as well as the efficiency desired. Generally, hydroformylations at reaction temperatures of greater than about 30° C., and preferably, greater than about 40° C., are suitable. Generally, hydroformylations at reaction temperatures of less than about 150° C., and preferably, less than about 120° C., are suitable. The total gas pressure of hydrogen, carbon monoxide, and olefin feedstock in the hydroformylation process is typically greater than about 1 psia (7 kPa) and, preferably, greater than about 8 psia (55 kPa), and more preferably, greater than about 10 psia (69 kPa). The total gas pressure of hydrogen, carbon monoxide, and olefin feedstock is typically less than about 500 psia (3447 kPa), preferably, less than about 300 psia (2068 kPa), and more preferably, less than about 100 psia (689 kPa). The carbon monoxide partial pressure of the hydroformylation process of this invention is typically greater than about 1 psia (7 kPa), preferably, greater than about 3 psia (21 kPa). The carbon monoxide partial pressure of the hydroformylation process of this invention is typically less than about 300 psia (2068 kPa), preferably, less than about 250 psia (1724 kPa), and more preferably, less than about 100 psia (689 kPa). The hydrogen partial pressure is typically greater than about 5 psia (35 psia), preferably, greater than about 10 psia (69 kPa). The hydrogen partial pressure is typically less than about 250 psia (1724 kPa), preferably, less than about 150 psia (1034 kPa). In general, the $H_2/CO$ molar ratio of gaseous hydrogen to carbon monoxide may be greater than about 1/10, and preferably, equal to or greater than about 1/1. The $H_2/CO$ molar ratio may be less than about 100/1, and preferably, equal to or less than about 10/1.

The hydroformylation process of this invention can be carried out in the liquid or gas phase, or preferably, in mixed liquid and gas phases, which can more preferably involve a continuous liquid phase containing the catalyst and a gas phase recycle system or a combination of recycle systems.

When the hydroformylation process of this invention is conducted as described hereinabove, then the conversions of α-olefin and β-olefin isomers are each greater than about 1.5 times the conversion of the iso-olefin isomer, as measured on the individual isomers under identical conditions. Preferably, the conversions of the α-olefin and β-olefin isomers are each greater than about 2 times the conversion of the iso-olefin, and more preferably, each greater than about 3 times the conversion of the iso-olefin, as measured on the individual isomers under identical conditions. For clarity of comparison, the conversion of each isomer is preferably measured individually in the absence of the other isomers under a controlled set of hydroformylation process conditions that are identical for each isomer evaluated. Use of the individual isomers rather than the mixture of isomers is preferred, primarily because isomerization of 1-butene to 2-butene and 2-butene to 1-butene may confuse the conversion measurements. By measuring conversions on the individual isomers, the true conversion of each isomer is accurately attained. More preferably, a specific set of hydroformylation process conditions is selected to be used in all of the conversion evaluation runs, including a specific $CO:H_2$ molar ratio, a specific CO partial pressure, a total pressure, a reaction temperature, a quantity of olefin or space velocity of olefin, a specific form of the calixarene bisphosphite ligand, a particular transition metal and quantity thereof, a total run time, and specific intervals of time at which aliquots of the reaction fluid are to be analyzed for conversion of the olefin. The analysis method of the reaction product fluid should also be identical for each isomer evaluated; for example, the same gas chromatographic column should be used under identical programming. In those cases wherein purified forms of the individual isomers are not readily available, the conversion evaluation can be run on a mixture of the isomers. In that instance, the conversions of each isomer can be estimated as best as possible.

The process of this invention unexpectedly achieves a high molar ratio of normal (or linear) to branched aldehyde products (N:I isomer ratio), as compared with prior art catalysts operating with similar raffinate feedstocks and reaction conditions. In this invention, the N:I isomer ratio depends upon the specific composition of the olefin feedstock and the extent of conversion, but typically the N:I isomer ratio is greater than about 3:1, preferably, greater than about 4:1, and more preferably, greater than about 6:1.

GLOSSARY OF TERMS

In the description hereinabove and in the claims that follow, reference is made to certain chemical terms, which shall be defined to have the following meanings.

As used herein, the phrase "having the formula" or "represented by the formula" is not intended to be limiting and is used in the same manner as the term "comprising" is commonly used.

The term "alkyl" as used herein refers to a linear, branched, or cyclic saturated hydrocarbon monovalent radical, typically, although not necessarily containing 1 to about 20 carbon atoms, for example, methyl, ethyl, n-propyl, isopropyl, n-butyl, t-butyl, octyl, decyl, and the like; as well as cycloalkyl groups, which typically contain from about 4 to about 8 carbon atoms, such as cyclopentyl, cyclohexyl, and cyclooctyl. The term "substituted alkyl" refers to any one of the aforementioned alkyl groups substituted with one or more substituents as noted hereinafter.

The term "alkoxy" as used herein refers to an alkyl group bound through a single, terminal ether linkage, that is, an alkoxy group may be represented by —O-alkyl, where alkyl is as defined hereinabove.

The term "aryl" as used herein refers to a monovalent aromatic radical containing a single aromatic ring or multiple aromatic rings that are fused together, directly linked, or indirectly linked (such that the different aromatic groups are bound to a common group such as a methylene or ethylene moiety). Preferred aryl groups contain one aromatic ring, or 2 to 4 fused or linked aromatic rings, for example, phenyl, naphthyl, biphenyl, and the like. The term "substituted aryl" refers to an aromatic group substituted with one or more substituents as noted hereinafter.

The term "aryloxy" as used herein refers to an aromatic group bound through a single, terminal ether linkage. An aryloxy may be represented by —O-aryl, where "aryl" is as defined hereinabove.

The term "aralkyl" or "arylalkyl" refers to an alkyl group having one or more aryl substituents.

The term alkaryl" or "alkylaryl" refers to an aryl group having one or more alkyl substituents.

The term "alicyclic" refers to an aliphatic cyclic moiety, which may be monocyclic, bicyclic, or polycyclic.

The word "substituents" or "substituted" as used herein shall include, without limitation, functional groups such as halogen, phosphonato, phosphoryl, phosphine, sulfinato, $C_{1-20}$ alkylsulfanyl, $C_{5-20}$ arylsulfanyl, $C_{1-20}$ alkylsulfonyl, $C_{5-20}$ arylsulfonyl, $C_{1-20}$ alkylsulfinyl, $C_{5-20}$ arylsulfinyl, sulfonamide, amino, amido, imino, nitro, nitroso, hydroxyl, $C_{1-20}$ alkoxy, $C_{5-20}$ aryloxy, $C_{2-20}$ alkoxycarbonyl, $C_{5-20}$ aryloxycarbonyl, carboxylate, mercapto, formyl, $C_{1-20}$ thioester, cyano, cyanato, carbamoyl, epoxy, styrenyl, silyl, silyloxy, silanyl, siloxazanyl, and the hydrocarbyl moieties $C_{1-20}$ alkyl, $C_{2-20}$ alkenyl, $C_{2-20}$ alkynyl, $C_{5-20}$ aryl, $C_{5-30}$ aralkyl, and $C_{5-30}$ alkaryl.

The term "amide" refers to substituents of the formula —C(O)NR$^{13}$R$^{14}$ or —CH$_2$C(O)NR$^{13}$R$^{14}$, wherein R$^{13}$ and R$^{14}$ are each independently selected from substituted and unsubstituted monovalent alkyl and aryl radicals, more preferably, substituted and unsubstituted $C_{1-15}$ monovalent alkyl radicals and $C_{6-25}$ monovalent aryl radicals.

The term "carbonyloxy" refers to a substituent of the formula —OC(O)R$^{15}$, such as acetoxy for —OC(O)CH$_3$, wherein R$^{15}$ is a substituted or unsubstituted monovalent $C_{1-15}$ alkyl or monovalent $C_{6-15}$ aryl group.

The term "alkoxycarbonyl" refers to a substituent of the formula —C(O)OR$^{15}$ such as methoxycarbonyl for —C(O)OCH$_3$, wherein R$^{15}$ is a substituted or unsubstituted monovalent $C_{1-15}$ alkyl or monovalent $C_{6-15}$ aryl group.

The term "keto" refers to a —C(O)R$^{15}$ group, wherein R$^{15}$ is a substituted or unsubstituted monovalent $C_{1-15}$ alkyl or monovalent $C_{6-15}$ aryl group.

The term "optional" or "optionally" means that the subsequently described circumstance may or may not occur. For example, the term "optionally substituted" means that a non-hydrogen substituent may or may not be present on a given atom, and thus, the description includes structures wherein a non-hydrogen substituent is present and structures wherein a non-hydrogen substituent is not present.

The following examples are illustrative of the present invention and are not to be regarded as limiting thereof. Based on the description and examples herein, variations in operational parameters, such as reactants, process conditions, species of transition metal-ligand complex catalyst, and calixarene bisphosphite ligands, falling within the scope of the claims will be apparent to those skilled in the art. All of the parts, percentages, and proportions referred to herein are given by weight, unless otherwise indicated.

Example 1

(a) Synthesis of 2,2'-biphenyl phosphoromonochloridite 2,2'-Biphenol (362.5 g, 1.908 mol) is charged to a 2-liter flask under a nitrogen gas atmosphere. Phosphorous trichloride (990.0 g, 7.21 mol) is added to the flask at room temperature, and the resulting mixture is heated slowly to reflux. A vigorous evolution of hydrogen chloride gas is observed at 38° C. Gas continues to evolve up to a temperature of 83.5° C. The mixture is then vacuum distilled, yielding 2,2'-biphenyl phosphoromonochloridite as an off-white solid (373.6 g, 1.49 mol; 78% yield). Analysis: $^{31}$P {1H} NMR (CDCl$_3$, 121.66 MHz) σ (PPM) 180.00.

(b) Synthesis of 2-bromo-N,N-diethylacetamide

Under a nitrogen atmosphere, a 1-liter flask is charged with 2-bromoacetylbromide (46.34 g, 230 mmol) and 300 ml ether. The flask is chilled to −15° C., and a solution of diethylamine (33.72 g, 460 mmol) in 200 ml ether is added over 1 hour to the flask. The resulting thick slurry is stirred cold for 1 additional hour, then warmed slowly to room temperature, and stirred overnight. The mixture is added to 250 ml cold water, and the resulting aqueous solution is extracted with ether (3 times, 200 ml ether each time). The combined ether extracts are washed with phosphoric acid (5 wt percent, 200 ml), aqueous potassium carbonate (8 wt percent, 200 ml) and thereafter brine (150 ml). The ether extract is then dried over sodium sulfate and concentrated in vacuo to a light brown residue. The residue is vacuum distilled to yield 2-bromo-N,N-diethylacetamide as a clear, colorless oil (22.99 g, 52% yield). $^1$H NMR (300 MHz, CDCl$_3$), δ (PPM): 1.08 (t, 3H), 1.20 (t, 3H), 3.33 (q, 4H), 3.79 (s, 2H).

(c) Synthesis of N,N-Diethylacetamide-p-tert-butylcalix[4]arene Diol

A suspension of p-tert-butylcalix[4]arene tetra-ol (15.00 g, 23.10 mmol, Aldrich Chemical Company) and potassium carbonate (3.51 g, 25.43 mmol) in acetonitrile (600 ml) is stirred at room temperature overnight. 2-Bromo-N,N-diethylacetamide (9.98 g, 50.90 mmol) is then added and the mixture is refluxed for 15 hours. The hot mixture is filtered to remove KBr, and the filtrate cooled to −20° C. to obtain 12.4 g (61% yield) of white crystals. $^1$H NMR (300 MHz, CDCl$_3$), δ (PPM): 6.93 (d, 8H), 4.85 (s, 4H), 4.50 (d, 4H), 3.46 (m, 8H), 3.30 (d, 4H), 1.27 (t, 6H), 1.18 (s, 24H), 1.09 (s, 18H).

(d) Synthesis of N,N-Diethylacetamide-p-tert-butylcalix[4]arene Bisphosphite Ligand A solution of 2,2'-biphenyl phosphoromonochloridite (1.15 g, 4.57 mmol) dissolved in tetrahydrofuran (5 ml) is added quickly with stirring and at room temperature to a solution of N,N-diethylacetamide-p-tert-butylcalix[4]arene diol (2.00 g, 2.29 mmol) and triethylamine (0.93 g. 9.14 mmol) dissolved in tetrahydrofuran (10 ml). A white precipitate forms immediately. The mixture is heated to reflux for 40 minutes. After the mixture is cooled to room temperature, the solid is filtered; the filtrate is evaporated; and the resulting solid product is triturated in acetonitrile (50 ml). The solid product is filtered and dried, and the filtrate is cooled to −30° C. to crystallize additional product, which is identified as N,N-diethylacetamide-p-tert-butylcalix[4]-arene bisphosphite. Total yield: 2.54 g, 88%. Analysis: $^{31}$P {1H} NMR (CDCl$_3$, 121.66 MHz) σ 127.61; $^1$H NMR (300 MHz, CDCl$_3$), δ (PPM): 7.41, 7.16 and 7.02 (16H, m, biphenyl protons); 6.94 (4H, s, calixarene); 6.54 (4H, s, calixarene); 4.93 and 3.19 (2×4H, d, JH-H=12.9 Hz, ArCH$_2$Ar); 4.62 (4H, s, OCH$_2$CONEt$_2$); 3.28 (8H, q, JH-H=7.5 Hz, CON(CH$_2$CH$_3$)$_2$); 1.23 and 0.89 (2×18H, s, t-Bu); 1.01 and 0.89 (2×6H, t, JH-H=7.5 Hz, CON(CH$_2$CH$_3$)$_2$); $^{13}$C NMR (75 MHz, CDCl$_3$), δ (PPM): 168.0 (CONEt$_2$); 152.9, 149.9, 146.2, 144.6, 134.5, 131.7, 131.0, 129.3, 128.7, 125.2 (d, JC-C=12.4 Hz); 124.3, 122.6 (aromatic carbons); 72.8 (OCH$_2$CONEt$_2$); 41.8 and 39.6 (CON(CH$_2$CH$_3$)$_2$); 34.0 and 33.7 (CMe$_3$); 32.8 (ArCH$_2$Ar); 31.8 and 31.2 (C(CH$_3$)$_3$); 14.3 and 12.9 (CON(CH$_2$CH$_3$)$_2$).

Example 2

The following procedure is conducted to measure the conversion of the individual isomers of butene in a hydroformylation process using a catalyst comprising rhodium and the calixarene bisphosphite ligand prepared in Example 1(d). Since butene-1 isomerizes to butene-2 and vice versa, accurate conversions of butene-1 and butene-2 are difficult to measure on an isomeric mixture. Accordingly, the conversions are more accurately measured on the hydroformylation of the individual isomers.

A rhodium catalyst precursor (dicarbonylacetylacetonato rhodium (I), 0.034 g, 300 ppm) and the N,N-diethylacetamide-p-tert-butylcalix[4]arene bisphosphite ligand of Example 1(d) (0.342 g, 2 equivalents/Rh) are weighed into a septum-capped bottle in a dry box. The solids are dissolved in tetraglyme, and the resulting solution transferred via vacuum into a 100 ml Parr mini-reactor. The catalyst-containing solution is then preheated with agitation (1100 rpm) to 85° C. under 1:1 carbon monoxide:hydrogen (syn gas) (45 psig, 310 kPa) for 20-30 minutes. A liquid olefinic isomer (9.4 g) is charged to an isolated section above the reactor, and pressured into the reactor with syn gas. A total reactor pressure of 200 psig (1379 kPa) [132 psi (or 910 kPa) 1:1 syn gas, corrected for olefin vapor pressure] is established with a Brooks model 5866 flow meter, and held constant throughout. Total gas uptake is measured with a Brooks 0151E totalizer. Liquid reaction samples are taken every hour and analyzed on an Agilent Technologies 6890 Gas Chromatograph (GC), equipped with a DB-1 30 m×0.32 mm, 1μ film column. Component quantization is based on GC area percent exclusive of solvent. The conversion of each butene isomer, namely, butene-1, cis-butene-2, trans-butene-2, and isobutene is tabulated in Table 1 and graphed as a function of time in FIG. 1.

TABLE 1

Conversion of Individual Isomers as a Function of Time

Figure 1:
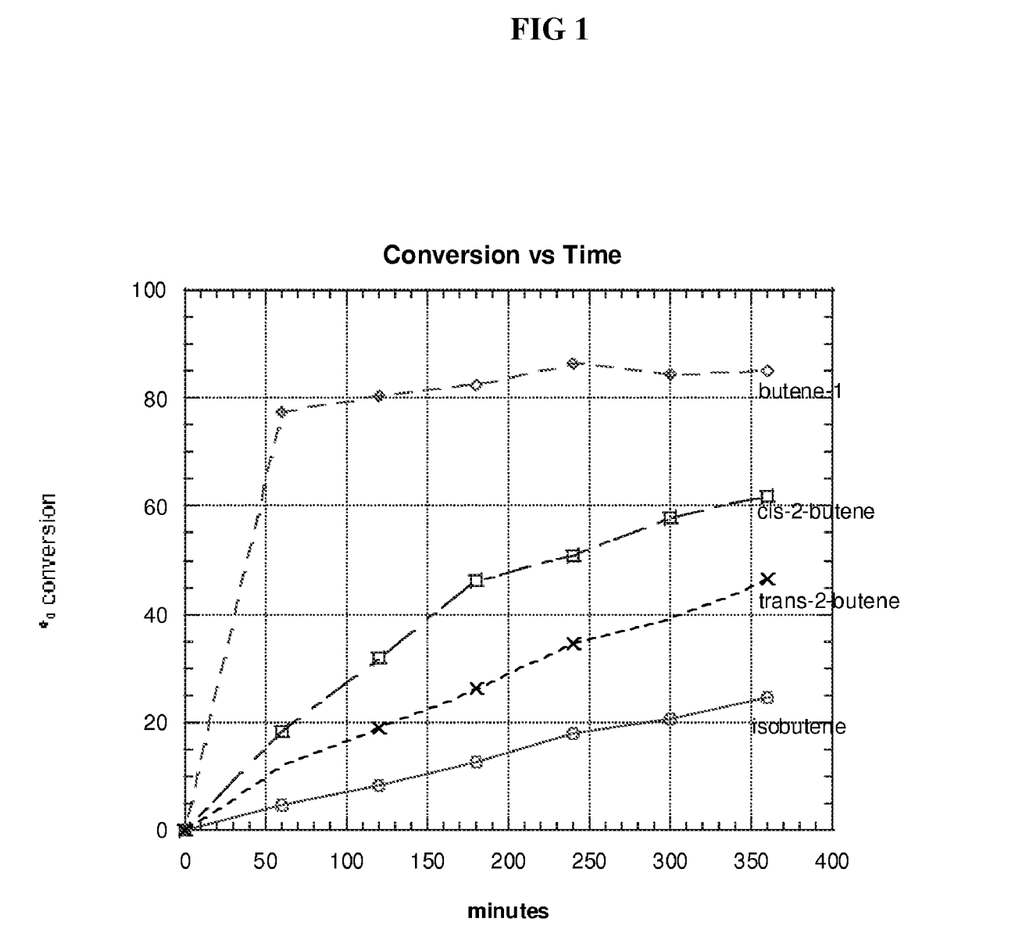
FIG. 1 is a graph of the conversions of butene-1, cis-butene-2, trans-butene-2 and isobutene as a function of time, as measured for each individual isomer in a hydroformylation process employing a rhodium-calixarene bisphosphite ligand complex catalyst of this invention.

| Time (h) | Isobutene | Butene-1 | Cis-Butene-2 | Trans-Butene-2 |
|---|---|---|---|---|
| 0 | 0.00 | 0.00 | 0.00 | 0.00 |
| 1 | 4.52 | 77.58 | 18.13 | 11.94 |
| 2 | 8.45 | 80.51 | 31.93 | 18.87 |
| 3 | 12.79 | 82.48 | 46.05 | 26.25 |
| 4 | 18.11 | 86.31 | 50.90 | 34.52 |
| 5 | 20.76 | 84.39 | 57.72 | 39.28 |
| 6 | 24.59 | 85.11 | 61.75 | 46.52 | a. Liquid isomer (9.4 g), CO:H$_2$ = 1:1; 85° C., 910 kPa.

It is seen that isobutene is converted at a significantly slower rate as compared with butene-1, cis-butene-2, and trans-butene-2.

Example 3

A hydroformylation of a butene raffinate stream is conducted as follows. A rhodium catalyst precursor (dicarbonylacetylacetonato) rhodium (I) (0.034 g, 300 ppm) and N,N-diethylacetamide-p-tert-butylcalix[4]arene bisphosphite ligand prepared in Example 1(d) (0.342 g, 2 eq/Rh) are weighed into a septum-capped bottle in a dry box. The solids are dissolved in tetraglyme (40.0 ml) to form a catalyst precursor solution. The precursor solution is transferred under vacuum into a 100 ml Parr mini-reactor. The solution is then preheated with agitation (1100 rpm) to a desired reaction temperature under 1:1 volume ratio of gaseous H$_2$:CO (syn gas) for 20-30 minutes. A C4 raffinate feedstream, obtainable from Shell Oil Company and having the composition shown in Table 2, is fed in liquid form (4.7 g) to an isolated section above the reactor and fed under pressure with syngas into the reactor.

TABLE 2

Composition of Raffinate Feed

| Raffinate 1 Feed | Composition |
|---|---|
| Methane, mol % | 0.01 |
| C2's, mol % | 0.01 |
| Propane, mol % | 0.1 |
| Propylene, mol % | 0.24 |
| i-Butane, mol % | 3.86 |
| n-Butane, mol % | 10.5 |
| Butene-1, mol % | 33.32 |
| Iso-Butene, mol % | 30.03 |
| trans-Butene-2, mol % | 12.81 |
| Cis-Butene-2, mol % | 8.66 |
| 1,3-Butadiene, mol % | 0.02 |
| 1,2-Butadiene, ppm | <100 |
| Propadiene, ppm | <100 |
| Methylacetylene, ppm | <100 |
| Ethylacetylene, ppm | <100 |
| Vinylacetylene, ppm | <100 |
| 3-Me-1-Butene, mol % | 0.01 |

The operating reactor pressure is established with a Brooks model 5866 flow meter and held constant throughout the run. Total operating pressure is 95 psia (648 kPa); operating temperature is 75° C. Total gas uptake and liquid reaction samples are analyzed as in Example 2. Results are shown in Table 3 and FIG. 2.

TABLE 3

Figure 2:
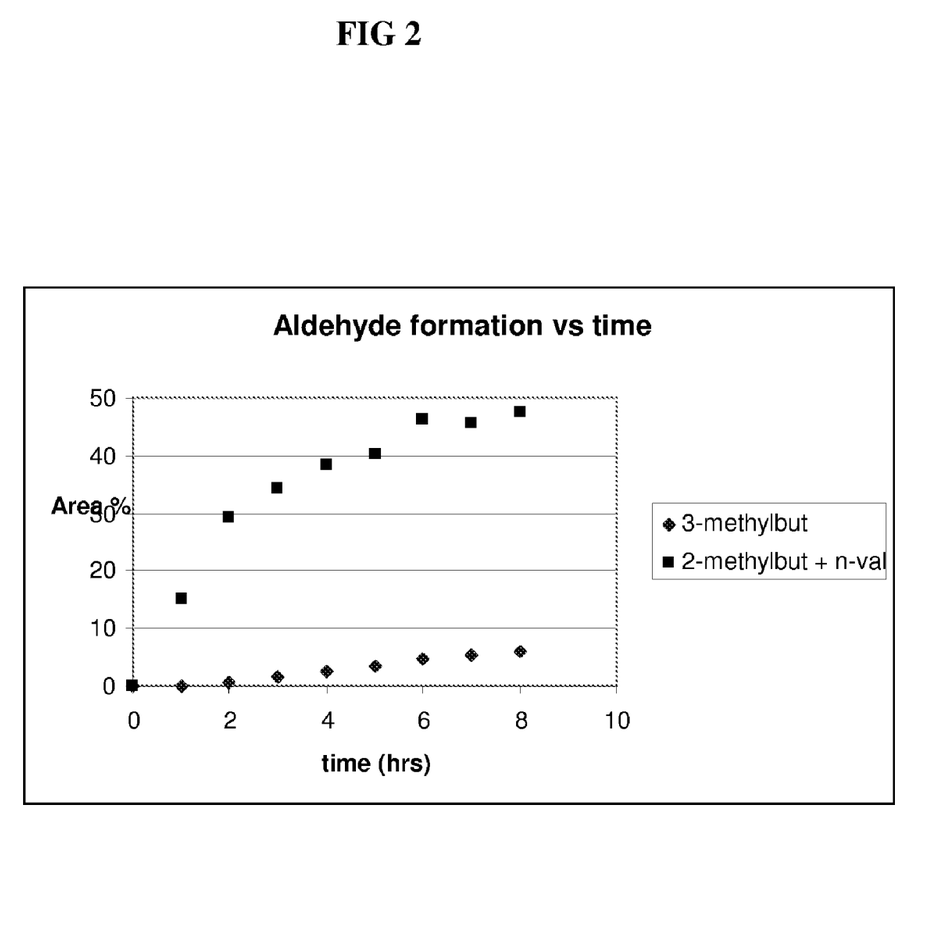
FIG. 2 is a graph of aldehyde products formation as a function of time in a hydroformylation process of a C4 raffi- nate feedstock further employing a rhodium-calixarene bisphosphite ligand complex catalyst of this invention.

GC Analysis (area %) of Aldehyde Product Mixture Obtained from Hydroformylation of Butene Raffinate

| Time (h) | 3-Me-butyraldehyde (3-MeBA) | 2-Me-butyraldehyde (2-MeBA) | n-valeraldehyde (n-VA) | 2MeBA + n-VA |
|---|---|---|---|---|
| 0 | 0.00 | 0.00 | 0.00 | 0.00 |
| 1 | 0.13 | 0.26 | 14.95 | 15.21 |
| 2 | 0.57 | 0.55 | 28.67 | 29.22 |
| 3 | 1.47 | 0.71 | 33.72 | 34.33 |
| 4 | 2.48 | 0.84 | 37.57 | 38.41 |
| 5 | 3.42 | 0.94 | 39.44 | 40.38 |
| 6 | 4.70 | 1.18 | 45.13 | 46.31 |
| 7 | 5.32 | 1.15 | 44.60 | 45.75 |
| 8 | 6.12 | 1.22 | 46.33 | 47.55 |

FIG. 2 illustrates a plot of the sum of the formation of 2-methylbutyraldehyde and n-valeraldehyde, which result from the conversion of butene-1 and cis and trans-butene-2, as compared with a plot of the formation of 3-methylbutyraldehyde, which results exclusively from the conversion of isobutylene, both plots shown as a function of time.

At 8 hours on stream, the results are as follows, based on area percent exclusive of solvent:
Selectivities:

| n-Valeraldehyde | 46.0 mole percent |
|---|---|
| 2-Methyl Butyraldehyde | 1.2 mole percent |
| 3-Methyl Butyraldehyde | 6.1 mole percent |

Unconverted Olefins and Saturated Hydrocarbons, Balance to 100 percent

Molar Ratios
n-Valeraldehyde:2-methylbutyraldehyde=38.1:1
n-Valeraldehyde:3-methylbutyraldehyde=7.6:1
n-Valeraldehyde:total branched aldehydes 6.3:1

What is claimed is:

1. A hydroformylation process comprising contacting a reactant mixture comprising isomeric olefins represented by the following formulas:

$RCH_2-CH_2-CH=CH_2$ (hereinafter, α-olefin reactant), $RCH_2-CH=CH-CH_3$ (hereinafter, β-olefin reactant), and $RCH_2-C(CH_3)=CH_2$ (hereinafter, iso-olefin reactant)

wherein each R is the same and is selected from the group consisting of hydrogen and $C_{1-4}$ monovalent alkyl radicals, with carbon monoxide and hydrogen in the presence of a transition metal-calixarene bisphosphite ligand complex catalyst, and optionally free calixarene bisphosphite ligand, under reaction conditions sufficient to form a hydroformylation product mixture comprising corresponding normal and branched isomeric aldehyde products, such that the α-olefin and β-olefin reactants achieve a conversion of greater than 1.5 times the conversion of the iso-olefin reactant; the calixarene bisphosphite ligand comprising the following formula:

wherein the calixarene is a calix[4]arene; each $R^1$, $R^2$, $R^3$, and $R^4$ is independently selected from the group consisting of hydrogen and substituted or unsubstituted $C_{1-20}$ alkyl radicals; each $Y^1$ and $Y^2$ is independently selected from the group consisting of substituted and unsubstituted monovalent alkyl, alkaryl, aralkyl, and amide radicals; and wherein each $Ar^1$, $Ar^2$, $Ar^3$, and $Ar^4$ is independently selected from substituted and unsubstituted monovalent $C_{6-20}$ aryl radicals, or alternatively, wherein $Ar^1$ and $Ar^2$ are connected to form a substituted or unsubstituted divalent $C_{12-25}$ arylene radical and/or $Ar^3$ and $Ar^4$ are connected to form a substituted or unsubstituted divalent $C_{12-25}$ arylene radical.

2. The process of claim 1 wherein the α-olefin reactant is butene-1, the β-olefin reactant is butene-2 (including cis and/or trans isomers), and the iso-olefin reactant is isobutene.

3. The process of claim 1 wherein the transition metal is selected from ruthenium, rhodium, cobalt, and iridium.

4. The process claim 1 wherein the process is conducted in the presence of a solvent selected from the group consisting of saturated hydrocarbons, aromatic hydrocarbons, ethers, aldehydes, ketones, nitriles, and aldehyde condensation products.

5. The process of claim 1 wherein the process is conducted in the presence of free calixarene bisphosphite ligand.

6. The process of claim 1 wherein the molar ratio of calixarene bisphosphite ligand to transition metal is greater than 1.2/1 and less than 100/1.

7. The process of claim 1 wherein the process is conducted at a temperature greater than 30° C. and less than 150° C.

8. The process of claim 1 wherein the process is conducted at a total pressure greater than 1 psia (7 kPa) and less than 500 psia (3,447 kPa).

9. The process of claim 1 wherein the carbon monoxide partial pressure is greater than 1 psia (7 kPa) and less than 300 psia (2,068 kPa); and wherein the hydrogen partial pressure is greater than 5 psia (35 psia) and less than 250 psia (1,724 kPa).

10. The process of claim 1 wherein the $H_2/CO$ molar ratio of gaseous hydrogen to carbon monoxide is greater than 1/10 and less than 100/1.

11. The process of claim 1 wherein the concentration of transition metal is greater than 10 ppm and less than 1,000 ppm.

12. The process of claim 1 wherein the calixarene bisphosphite ligand is represented by the following formula:

13. The process of claim 1 wherein the normal to branched aldehyde product ratio is greater than 4:1, and optionally, wherein the conversion of the α-olefin and/or β-olefin reactant is greater than 2 times the conversion of the iso-olefin reactant.

14. A novel calixarene bisphosphite composition represented by the following formula:

wherein the calixarene is a calix[4]arene; each $R^1$, $R^2$, $R^3$, and $R^4$ is independently selected from the group consisting of hydrogen and substituted or unsubstituted monovalent $C_{1-20}$ alkyl radicals; each $Y^1$ and $Y^2$ is independently selected from the group consisting of substituted and unsubstituted monovalent alkaryl, aralkyl, and amide radicals; and each $R^6$, $R^7$, $R^8$, $R^9$, $R^{10}$, $R^{11}$, $R^{6'}$, $R^{7'}$, $R^{8'}$, $R^{9'}$, $R^{10'}$, and $R^{11'}$ is independently selected from hydrogen, $C_{1-20}$ alkyl, $C_{7-20}$ alkaryl, $C_{1-20}$ alkoxy, $C_{6-20}$ aryloxy, —C(O)$R^{15}$, —C(O)O$R^{15}$, and —OC(O)$R^{15}$ wherein $R^{15}$ is a substituted or unsubstituted monovalent $C_{1-15}$ alkyl or monovalent $C_{6-15}$ aryl group, and wherein $R^5$, $R^{5'}$, $R^{12}$, and $R^{12'}$ are each individually selected from hydrogen and $C_{1-3}$ primary alkyl groups.

15. The composition of claim 14 wherein $Y^1$ and $Y^2$ are each amide radicals; wherein $R^1$, $R^2$, $R^3$ and $R^4$ are each selected from monovalent $C_{1-20}$ alkyl radicals; and wherein each $R^5$, $R^6$, $R^7$, $R^8$, $R^9$, $R^{10}$, $R^{11}$, $R^{12}$, $R^{5'}$, $R^{6'}$, $R^{7'}$, $R^{8'}$, $R^{9'}$, $R^{10'}$, $R^{11'}$, and $R^{12'}$ is hydrogen.

16. The composition of claim 14 comprising a ligand represented by the following formula:

17. A complex catalyst or complex catalyst precursor composition comprising a transition metal bonded to the calixarene bisphosphite ligand of claim 14, the transition metal optionally being further bonded to carbon monoxide, hydrogen, or both carbon monoxide and hydrogen.

18. The complex catalyst or complex catalyst precursor composition of claim 17 wherein the transition metal is ruthenium, rhodium, cobalt, or iridium.

19. A complex catalyst solution or complex catalyst precursor solution comprising a solvent, a complex catalyst or catalyst precursor composition comprising a transition metal bonded to the calixarene bisphosphite ligand, and optionally, free calixarene bisphosphite ligand, the aforementioned calixarene ligand being represented by the calixarene ligand of claim 14; and wherein optionally, the transition metal may be further bonded to carbon monoxide, hydrogen, or both carbon monoxide and hydrogen.

20. The process of claim 1 wherein the olefin comprises from about 25 to about 80% 1-butene, from about 5 to about 40% trans-2-butene, from about five to about 25% cis-2-butene, from about 0.5 to about 40% of isobutene, from about 5 to about 20% n-butene, and from about 0.5 to 5% isobutane, wherein the total moles of olefin is 100 mole percent.

* * * * *